United States Patent [19]

Suhara et al.

[11] 4,273,765
[45] Jun. 16, 1981

[54] AMINO SUGAR DERIVATIVES CONTAINING TREHALOSE

[75] Inventors: Yasuji Suhara; Kiyoshi Ogawa, both of Yokohama; Kazuteru Yokose, Urayasu; Kimihiro Watanabe, Ayase, all of Japan

[73] Assignee: Hoffmann-La Roche Inc., Nutley, N.J.

[21] Appl. No.: 11,002

[22] Filed: Feb. 9, 1979

[30] Foreign Application Priority Data

Feb. 14, 1978 [GB] United Kingdom ............... 5834/78

[51] Int. Cl.³ .................... A61K 31/73; C07H 5/06
[52] U.S. Cl. .................................. 424/180; 536/1; 536/4; 536/18; 435/84
[58] Field of Search ................ 536/18, 4; 424/180

[56] References Cited

U.S. PATENT DOCUMENTS

Re. 29,903  2/1979  Kirby et al. ............... 536/18
4,062,950  12/1977  Frommer et al. .......... 536/18
4,065,557  12/1977  Frommer et al. .......... 536/18

FOREIGN PATENT DOCUMENTS 2347782  4/1975  Fed. Rep. of Germany ....... 536/18
7147019  8/1972  France ........................... 536/18
7431906  4/1975  France ........................... 536/18
7709939  10/1977  France ........................... 536/18

OTHER PUBLICATIONS

Masahika "Chem. Abst.", vol. 70, 1969, p. 1958(a).

Primary Examiner—Johnnie R. Brown
Attorney, Agent, or Firm—Jon S. Saxe; George M. Gould; William H. Epstein

[57] ABSTRACT

This invention relates to Trestatin A, Trestatin B and Trestatin C salts thereof and mixtures thereof as well as compositions containing at least one of the Trestatins A, B or C or a salt thereof. These compositions are useful for the inhibition of sucrase and inhibition of alpha-amylase.

2 Claims, 8 Drawing Figures

AMINO SUGAR DERIVATIVES CONTAINING TREHALOSE

SUMMARY OF THE INVENTION

In accordance with this invention, it has been discovered that novel amino sugar derivatives selected from the group consisting of: Trestatin A, Trestatin B, Trestatin C salts and mixtures thereof are amylase-inhibiting agents. In view of their activity as amylase inhibitors, these amino sugar derivatives are useful as agents for treatment of diabetes, obesity, hyperlipidemia and atheriosclerosis as well as agents useful in the present and/or reduction of caries formation.

The Trestatins of this invention can be produced by cultivating, under aerobic conditions in an aqueous mixture, a microorganism of the genus Streptomyces which is capable of producing Trestatins.

DETAILED DESCRIPTION OF THE INVENTION

The present invention relates to novel amino sugar derivatives having trehalose as a common structural feature, and salts thereof.

In the following, the amino sugar derivatives of this invention are called "Trestatins".

The invention relates further to a process for the preparation of the Trestatins and to amylase-inhibiting compositions containing one or more of the Trestatins or salts thereof.

More particularly, the invention relates to Trestatin A, Trestatin B and Trestatin C, their salts and mixtures thereof as well as to compositions containing at least one of the Trestatins A, B or C or a salt thereof.

Trestatin A, Trestatin B and Trestatin C are basic white powders having the following physicochemical properties:

(a) Elementary analysis:

|  | C % | H % | N % | O % |
| --- | --- | --- | --- | --- |
| Trestatin A: | 46.72 | 7.13 | 2.08 | 43.28 |
| Trestatin B: | 46.27 | 7.04 | 1.65 | 44.69 |
| Trestatin C: | 47.55 | 7.15 | 2.29 | 42.66 |

(b) Molecular weight (Osmometry):
Trestatin A: 1470
Trestatin B: 975
Trestatin C: 1890

(c) Melting point:
Trestatin A: 221°–232° C. (dec.)
Trestatin B: 209°–219° C. (dec.)
Trestatin C: 230°–237° C. (dec.)

(d) Specific rotation:
Trestatin A: $[\alpha]_D^{24} = +177°$ (c=1.0, $H_2O$)
Trestatin B: $[\alpha]_D^{26} = +187°$ (c=1.0, $H_2O$)
Trestatin C: $[\alpha]_D^{23} = +169.5°$ (c=1.0, $H_2O$)

(e) Ultraviolet absorption spectrum (in water):
Each of Trestatin A, Trestatin B and Trestatin C shows end absorption (f) Infrared absorption spectrum (in KBr):
Trestatin A: as shown in FIG. 1
Trestatin B: as shown in FIG. 2
Trestatin C: as shown in FIG. 3

(g) $1_H$ NMR spectrum (in $D_2O$ at 100 MHz)
Trestatin A: as shown in FIG. 4
Trestatin B: as shown in FIG. 5
Trestatin C: as shown in FIG. 6

(h) Solubility in solvents:
Trestatin A, Trestatin B and Trestatin C and their hydrochlorides are easily soluble in water; soluble in dimethylsulfoxide, slightly soluble in ethanol and acetone; and insoluble in ethyl acetate and chloroform;

Color reaction:
Each of Trestatin A, Trestatin B and Trestatin C is positive to permanganate and anthrone reactions, and negative to Sakaguchi reaction.

According to the present invention, the novel Trestatins, i.e. Trestatin A, Trestatin B and Trestatin C are prepared by a process which comprises cultivating a Trestatins-producing microorganism belonging to the genus Streptomyces under aerobic conditions in an aqueous medium, recovering the Trestatins from the fermentation broth, and, if required, separating, Trestatin A, Trestatin B and Trestatin C from each other.

The Trestatins-producing microorganisms used according to the present invention include all strains belonging to the genus Streptomyces which are capable of producing Trestatins as well as mutants and variants thereof. Among this genus *Streptomyces dimorphogenes* are preferred. Particularly preferred strains thereof are *Streptomyces dimorphogenes* NR-320-OM7HB and *Streptomyces dimorphogenes* NR-320-OM7HBS which were isolated from soil in Chichibu-shi, Saitama-ken, Japan as well as mutants and variants thereof.

The strains, *Streptomyces dimorphogenes* NR-320-OM7HB and *Streptomyces dimorphogenes* NR-320-OM7HBS have been deposited in the Agency of Industrial Science and Technology, Fermentation Research Institute, Japan, under "FERM-P No. 3664" and "FERM-P No. 3665" respectively. *Streptomyces dimorphogenes* NR-320-OM7HB has also been deposited at the American Type Culture Collection, Rockville, Md. under ATCC No. 31484; *Streptomyces dimorphogenes* NR-320-OM7HBS has also been deposited at the American Type Culture Collection, Rockville, Md. under ATTC No. 31485. The mycological characteristics of these strains are as follows:

I. Morphology

Microscopically, FERM-P No. 3664 develops dominantly straight and rarely spiral aerial mycelia with 10–50 spores per chain from well-branched substrate mycelia on various ISP media. The spores were smooth in surface and ranged 0.6–1.0×0.8–1.4μ. Neither whorl branching nor sporeangium formation was recognized. Furthermore, during the observation of its aerial mycelium morphology, a small population (less than 1%) with spiral aerial mycelia was found to exist as a cluster among dominant population with straight spore chain. When the spiral colony was singly isolated, the clone was found to maintain its spiral aerial mycelium morphology over generations, with producing constantly a small portion (0.7-2%) of straight aerial mycelium clusters or colonies. This substrain obtained by singly isolating the spiral colony from the strain of FERM-P 3664 is given the designation FERM P-3665. No distinct difference was recognized in the characteristics between FERM P-3664 and FERM P-3665 except for the morphology of each aerial mycelium.

II. Cultural characteristics

Both strains, FERM P-3664 and FERM P-3665 have the same cultural characteristics as mentioned in Table 1. All tests were done with cultures grown at 27° except that the skim milk test was performed at 37° C. Color determinations were made with 14–21 days old cultures according to the Color Harmony Manual, 4th ed. 1958 (Container Cooperation of America, Chicago).

TABLE I.

| Medium | Aerial mycelium | Substrate mycelium | Reverse-substrate mycelium | Soluble pigment |
|---|---|---|---|---|
| Sucrose-nitrate agar | brownish white ~ light gray [3dc, Natural] | good, pale yellowish brown ~ grayish yellow brown [31g, Lt Brown] | yellowish brown [3ng, Yellow maple] ~ dark brown [4pl, Deep Brown] | brownish |
| Glucose-asparagine agar | thin, brownish gray | moderate, pale yellowish brown [21e, Old Gold] ~ dull yellowish orange | pale yellowish brown [21e, Old Gold] ~ dull yellowish orange | none |
| Glycerol-asparagine agar (ISP med. 5) | grayish white ~ light gray [2dc, Natural ~ 2fe, Covert Gray] | good, grayish yellow brown ~ yellowish brown [3ng, Yellow Maple] | grayish yellow brown ~ dark yellowish brown [3ni, Clove Brown] | brown |
| Inorganic salts-starch agar (ISP med. 4) | light gray [2fe, Covert Gray] ~ light brownish gray [3fe, Silver Gray] | good, yellowish brown ~ brown [31g, Cinnamon Brown] | yellowish brown ~ brown [31g, Cinnamon Brown] | brown |
| Tyrosine agar (ISP med. 7) | light gray [2dc, Natural ~ 2fe, Covert Gray] ~ gray | good, pale brown ~ yellowish brown [3ng, Yellow Maple] | pale brown ~ yellowish brown [3ng, Yellow Maple] | faint brownish |
| Nutrient agar | thin, white ~ | poor, pale yellowish brown | colorless ~ pale yellowish brown | none |
| Yeast extract-malt extract agar (ISP med. 2) | light gray [2fe, Covert Gray] ~ light brownish gray [3fe, Silver Gray] | moderate ~ good, grayish yellow brown ~ brown [31g, Cinnamon Brown] | grayish yellow brown ~ brown [31 g, Cinnamon Brown] | faint brownish |
| Oatmeal agar (ISP med. 3) | light gray [2fe, Covert Gray] ~ light brownish gray [3fe, Silver Gray] | good, pale yellow ~ pale yellowish brown [2gc, Bamboo ~ 2ie, Lt Mustard Tan] | pale yellow ~ pale yellowish brown [2gc, Bamboo ~ 2ie, Lt Mustard Tan] | yellowish |
| Skim milk-nutrient agar | none | colorless ~ pale yellow | colorless ~ pale yellow | none |
| Glucose-peptone gelatin stab | none | colorless ~ pale yellow | — | none |
| Skim milk (37° C.) | thin, white | brownish gray ~ pale brown | — | none |

TABLE II.

Comparison of morphological, cultural and physiological characteristics of strain NR-320-CM71D: , NR-320-OX/MOS and related strains.

| | NR-320-CM7HB | NR-320-CM-7HBS | S. nigrifaciens ISP 5071 | S. olivaceus ISP 5072 | S. plicatus ISP 5019 |
|---|---|---|---|---|---|
| Morphological Section (ISP med. 2,3,4,5) | RF[a], (S) | S[b], (RF) | RF | S, RA[c], RF | S, RA |
| Spore surface ISP medium 3 | smooth | smooth | smooth | smooth | smooth |
| a.m.[d] | abundant | abundant | abundant | thin | moderate, spreading |
| | light gray ~ light brownish gray | light gray ~ light brownish gray | olive gray | light brownish gray | light brownish gray |
| s.m.[e] | pale yellow ~ pale yellowish brown | pale yellow ~ pale yellowish brown | greenish yellow ~ dark yellow | pale yellowish brown | greenish yellow brown |
| r.s.m.[b] | pale yellow ~ pale yellowish brown | pale yellow ~ pale yellowish brown | dull yellow | colorless ~ pale yellowish brown | pale yellowish brown |
| s.p.[g] | yellowish | yellowish | yellow | none | none |
| ISP medium 4 a.m. | abundant | abundant | abundant | thin | moderate, spreading |
| | light gray ~ light brownish gray | light gray ~ light brownish gray | light brownish gray | light brownish gray | light brownish gray |
| s.m. | yellowish brown ~ brown | yellowish brown ~ brown | dark yellow ~ yellowish brown | pale yellowish brown ~ dark yellowish brown | yellowish brown ~ dark yellowish brown |
| r.s.m. | yellowish brown brown | yellowish brown brown | yellowish brown | pale yellow ~ pale yellowish brown | yellowish brown |
| s.p. | brown | brown | brown | none | none |
| Melanin formation[A] | | | | | |

TABLE II.-continued

Comparison of morphological, cultural and physiological characteristics of strain NR-320-CM71D:, NR-320-OX/MOS and related strains.

| | NR-320-CM7HB | NR-320-CM-7HBS | S. nigrifaciens ISP 5071 | S. olivaceus ISP 5072 | S. plicatus ISP 5019 |
|---|---|---|---|---|---|
| on ISP medium 1 | (−) | (−) | − | − | − |
| on ISP medium 6 | − | − | − | − | − |
| on ISP medium 7 | (−) | (−) | − | − | − |
| Carbon utilization[B] | | | | | |
| L-arabinose | ++ | ++ | + | ++ | ++ |
| D-xylose | ++ | ++ | + | + | ++ |
| D-glucose | ++ | ++ | ++ | ++ | ++ |
| D-fructose | ++ | ++ | ± | + | ++ |
| sucrose | ++ | ++ | − | − | − |
| I-inositol | ++ | ++ | − | ± | ++ |
| rhamnose | ++ | ++ | ++ | ++ | ++ |
| raffinose | ++ | ++ | − | − | − |
| D-mannitol | ++ | ++ | ++ | ++ | ++ |
| Casein hydrolysis[C] | + | + | + | + | + |
| Starch hydrolysis | + | + | + | + | + |
| Gelatin liquefaction | + (poor) | + (poor) | + (poor) | + (poor) | − |
| Nitrate reduction | − | − | − | − | − |
| Milk coagulation | − | − | + | − | + |
| Milk peptonization | +(strong) | +(strong) | +(strong) | +(strong) | +(strong) |
| Temperature range of growth on ISP-2 (°C) | 20~45 | 20~45 | 20~37 | 20~37 | 20~45 |

[a] rectiflexibiles
[b] spirales
[c] retinaculiaperti
[d] aerial mycelium
[e] substrate mycelium
[f] reverse-substrate mycelium
[g] soluble pigment
[h] −; not formed, (−) probably not formed.
[B] ++; good utilization, + utilization, ± probable utilization, − no utilization.
[C] + positive, − negative.

III. Physiological properties

No distinct difference was recognized in the following characteristics between strains FERM-P No. 3664 and 3665.

(1) Temperature range of growth

When tested on ISP-2 medium, moderate to abundant growth was observed at 20°, 25° C., 27° C., 30° C., 37° C. and 45° C., but not at 6° C. and 55° C. Optimal temperature for growth was found at around 37° C.

(2) Gelatin liquefaction on glucose-peptone-gelatin agar cultured at 27° C.

The liquefaction was positive after around day 12 and its intensity was poor.

(3) Starch hydrolysis on inorganic salts-starch agar cultured at 27° C.

The hydrolysis was positive but medium in its intensity.

(4) Coagulation and peptonization in 10% skim milk medium at 37° C.

The peptonization became positive at around day 5 and its intensity was strong. The coagulation was negative.

(5) Casein hydrolysis on 10% skimmed milk-nutrient agar at 27° C.

The hydrolysis was positive with moderate to strong intensity.

(6) Nitrate reduction on ISP-8 medium at 27° C.
Negative.

(7) Melanin formation cultured at 27° C.

No pigment is formed on peptone-yeast-iron agar (ISP-6). It was also judged negative on both trypton-yeast broth (ISP-1) and tyrosine agar (ISP-7).

(8) Utilization of carbohydrates on Pridham-Gottlieb agar medium (ISP-9) cultured at 27° C.

Abundant growth was seen with L-arabinose, D-xylose, D-glucose, D-fructose, sucrose, inositol, raffinose, D-mannitol and L-rhamnose.

The summary of the above mentioned microbiological properties of the strains "FERM-P No. 3664 and 3665" is as follows:

Said strain is an Actinomycetales belonging to the genus Streptomyces and the form of aerial mycelia thereof is straight and spiral (Dominantly straight with NR-320-OM7HB and dominantly spiral with NR-320-OM7HBS). No whorl formation was recognized. Spores of both strains were smooth in surface and ranged 0.6–1.0×0.8–1.4μ. The strains developed light gray to light brownish gray aerial mycelia from pale yellowish brown to yellowish brown growth on various ISP media with brownish soluble pigment. Melanoid pigment was not produced on peptone-yeast-iron agar, probably not produced on tryptone-yeast broth and tyrosine agar. They strongly peptonized skim milk. Gelatin liquefaction was poor, while they hydrolyzed starch to a moderate extent. No difference between NR-320-OM7HBS and NR-320-OM7HB was recognized in all tests carried out as above.

These characteristics suggest that the strains resemble S. nigrifaciens [Waksman, S. A. (1961) Classification, identification and description of genera and species, The Actinomycetes Vol. 2, The Williams and Wilkins Co., Baltimore. Shirling, E. B. & D. Gottlieb (1968) Cooperative description of type culture of Strepytomyces, II. Species descriptions from the first study, Inst. J. Syst. Bacteriol., 18:69–189. Buchanan, R. E. & N. E. Gibbons (1974) Bergey's Manual of Determinative Bacteriology, 8th ed., The Williams and Wilkins Co., Baltimore. Waksman, S. A. (1919) Cultural studies of species of Actinomyces, Soil Sci., 8:167–171.], S. olivaceus [Waksman, S. A. (1961) Classification, identification and description of genera and species, The Acyinomycetes Vol. 2, The Williams and Wilkins Co., Baltimore. Shirling, E. B. & D. Gottlieb (1968) Cooperative description of type culture of Streptomyces, II. Species descriptions from the first study, Inst. J. Syst. Bacteriol., 18:69–189. Buchanan, R. E. & N. E. Gibbons (1974) Bergey's Manual of Determinative Bacteriology, 8th ed., The Williams and Wilkins Co., Baltimore. Waksman, S. A. (1919) Cultural studies of species of Actinomyces, Soil Sci., 8:167–171. Breed, R. S., E. G. D. Murray & N. R. Smith (1957) Bergey's Manual of Determinative Bacteriology, 7th ed., The Williams and Wilkins Co., Baltimore.] and *S. plicatus* [Buchanan, R. E. & N. E. Gibbons (1974) Bergey's Manual of Determinative Bacteriology, 8th ed., The Williams and Wilkins Co., Baltimore. Shirling, E. B. & D. Gottlieb (1969) Cooperative description of type culture of Streptomyces, IV. Species descriptions from the second, third and fourth studies, Inst. J. Syst. Bacteriol., 19:391–512. Parke, Davis and Co. (1954) Antiobiotics and methods for obtaining same, British Pat. Specification No. 707,332 April 14, Pat. Office, London.]. The comparison of the present strains with those obtained from ISP is shown in Table II. It was evidenced that NR-320-OM7HB as well as substrains of different a.m. morphology NR-320-OM6HBS are differentiable from either of these three closely related species.

In comparison with *S. nigrifaciens*, NR-320-OM7HB differs from it in coagulation of skim milk and the utilization of sucrose, inositol and raffinose. Morphologically, *S. nigrifaciens* never formed spiral. These facts, together with the production of olive gray aerial mycelium, greenish yellow substrate mycelia on ISP-3 medium and incapability of the inhibitor production, render it unlikely that both strains belong to identical species.

On the other hand, spore chain of *S. plicatus* ISP 5319 mainly appears spiral in form of ISP-2, 3, 4 and 5 media. Although loop-shaped aerial mycelium was less frequently observed, no straight form was recognized with ISP 5319, which differentiates *S. plicatus* from NR-320-OM7HB. Furthermore, distinct differences were seen in spreading of aerial mycelium, pigmentation, coagulation, gelatin liquefaction and the utilization of sucrose and raffinose.

*S. olivaceus* was found to be most clearly related to NR-320-OM7HB among the three species examined. Thus, *S. olivaceus* ISP 5072 showed spiral formation in most parts on ISP-2, 3, 4, and 5 media, containing partly loop-shaped-straight spore chains at aerial mycelium. However, it differs from either NR-320-OM7HB or NR-320-OM7HBS in that both spiral, loop-shaped and straight spore chains co-exist within one cluster of ISP 5072 aerial mycelium, which was never observed with NR-320OM7HB and NR-320-OM7HBS. Between ISP 5072 strain and strain NR-320-OM7HB, further differences were observed in production of soluble pigment (no pigmentation by ISP 5072 strain on ISP-2, 3, 4 and 5 media), development of aerial mycelium (thin aerial mycelium with ISP 5072), utilization of carbon source (sucrose/raffinose) and production of α-amylase inhibitor (no inhibition by ISP 5072 metabolites. All these results evidenced that NR-320-OM7HB as well as NR-320-OM7HBS seemed to be most closely related to, but not to be identical with species *S. olivaceus* ISP 5072.

It therefore appears justified to recognize this taxon as a new species in the genus Streptomyces and it is proposed to name this as *Streptomyces dimorphogenes* nov. sp. WATANABE and MARUYAMA, 1978. The type strain of *S. dimorphogenes* is NR-320-OM7HB (FERM-P No. 3664). Etymology: di (dual), (Gr.), morphe' (form) + genesis, is based on the occurrence of two forms in spore chain morphology, i.e. the patchy distribution of spiral chained cluster as minority. A biotype, NR-320-OM7HBS (FERM-P No. 3665) in which spiral spore chain is dominant with patchy distribution of straight spore chain as minor cluster, would then be suitable to be named as *S. dimorphogenes* subsp. *spiroformatus*, in relation to the aerial mycelium morphology. Accordingly, the type strain FERM-P No. 3664 should be called as *S. dimorphogenes* subsp. *dimorphogenes*.

According to the present invention, the Trestatins can be produced by cultivating the Trestatins-producing microorganism belonging to the genus Streptomyces as mentioned above, e.g. *Streptomyces dimorphogenes* sp. nov.; Watanabe & Maruyama (NR-320-OM7HB, FERM-P No. 3664) or *Streptomyces dimorphogenes* subsp. *spiroformatus* (NR-320-OM7HBS, FERM-P No. 3665) under aerobic conditions in an aqueous medium.

The cultivation may be performed in a culture medium containing usual nutrient substances which the microorganism used in the present invention can utilize. The carbon sources, for example, are starch, dextrin, glucose, glycerol, sucrose, trehalose, molasses or a mixture thereof; and the nitrogen sources are e.g. soybean powder, meat extract, peptone, yeast extract, cornsteep liquor, ammonium sulfate, sodium nitrate, ammonium chloride or a mixture thereof. Furthermore, if necessary, the culture medium may contain suitable inorganic substances such as calcium carbonate, sodium chloride and the like; and/or salts of zinc, copper, manganese, iron and the like. In addition, an antifoam agent such as silicone, vegetable oil and the like may be added to the culture medium in order to prevent foaming during the cultivation.

The cultivation may be effected under aerobic condition in an aqueous medium, especially by a submerged fermentation process. The pH of the medium at the beginning of the cultivation is about 7. The preferred temperature for the cultivation is in the range of 20° to 40° C., in particular 25°–30° C.

When the cultivation is carried out for about 1–5 days under the conditions mentioned above, the Trestatins can be obtained in the fermentation broth. The cultivation is suitably terminated at the time when the maximum potency of the Trestatins has been attained. The amount of Trestatins obtained is determined by the following method:

DETERMINATION OF THE TRESTATINS

The Trestatins have strong α-amylase inhibitory activity. Therefore, they can be determined by a method utilizing the assay of α-amylase by P. Bernfeld (Methods in Enzymology, I, 149, 1955) as mentioned below.

2 units* of porcine pancreatic α-amylase in 0.1 ml of 6.4 mM ammonium sulfate solution are added to 0.6 ml of 20 mM phosphate buffer (pH 6.9) containing 10 mM sodium chloride and different amounts of Trestatin. The mixture, after equilibration at 37° C. for 5 min. followed by the addition of 0.5 ml of 4% soluble starch solution, is incubated for 5 min. at 37° C. The reaction is terminated by the addition of 2 ml of dinitrosalicylic acid reagent prepared according to the method of P. Bernfeld. The mixture is heated on a boiling water bath for 5 min. and then diluted with 10 ml of water. Absorbance ($A_1$) of the resulting colored solution is measured at 540 nm, and the inhibition of α-amylase activity can be calculated from the following equation:

$$\text{Inhibition} = (1 - \frac{A_1 - A_0}{A_2 - A_0}) \times 100 \, (\%)$$

$A_0$; absorbance without enzyme
$A_2$; absorbance without Trestatin

*1 unit of the α-amylase is the amount of enzyme which catalyzes under the above conditions without Trestatin the formation of reducing sugars equivalent to 1 μmol of maltose.

The inhibition unit (IU) is defined as the amount of Trestatin which gives 50% inhibition of the enzyme under the above described assay conditions.

After the cultivation, the isolation of the Trestatins produced in the fermentation broth may be effected by using methods known per se such as the following: From the fermentation broth obtained in the manner described above, the mycelia are removed by centrifugation or filtration. Trestatins are water-soluble, weakly basic compounds. Therefore, conventional methods frequently used in the isolation and purification of a water-soluble, basic substance can be utilized in order to isolate and purify the Trestatins. For example, the isolation and purification of the Trestatins from the filtrate, can be carried out by means of adsorption methods using an adsorbent such as activated carbon, cation exchange resin and the like; precipitation methods using a solvent such as alcohol, acetone and the like; chromatography methods using cellulose, Sephadex (the trade name of Pharmacia Co.) and the like; or combinations thereof.

The isolation of Trestatin A, Trestatin B and Trestatin C respectively in a form of the single compound from the fermentation-filtrate may be carried out by means conventional in the art. In accordance with a preferred embodiment, separation is conveniently effected by column chromatography utilizing a mixture of H-form and ammonium-form of a weakly acidic cation exchange resin. One of the preferable embodiment is as follows:

The pH of the fermentation filtrate is adjusted to pH 7 with an alkali such as sodium hydroxide, potassium hydroxide, sodium carbonate, potassium carbonate and the like. To the filtrate is added activated carbon to adsorb the Trestatins and the mixture is filtered. The Trestatins are eluted from the carbon cake with 30–70%, preferably 50% of aqueous acetone. The eluting agent is preferably adjusted to pH 1–3 with an acid and the elution is carried out at 50°–70° C. The eluate is concentrated and the concentrate is passed through a column of a cation exchange resin, such as Dowex 50 (H-form, the trade name of Dow Chemical Co.) to adsorb the Trestatins. The column is washed with water and eluted with 1 N aqueous ammonia. The fractions exhibiting amylase inhibitory activity are collected, concentrated in vacuo and lyophilized to obtain a crude powder containing the Trestatins. The crude powder is treated with methanol to remove methanol-soluble impurities. The Trestatins are almost insoluble in methanol. The methanol-insoluble powder containing the Trestatins is dissolved in water. The solution is passed through a column packed with an anion exchange resin, such as Dowex 1 (acetate-form, the trade name of Dow Chemical Co.). The column is developed with water and the eluate is fractionated. The active fractions are collected, concentrated under reduced pressure and passed through a column filled with a cation exchange resin, such as Dowex 50 (ammonium-form, the trade-name of Dow Chemical Co.). The column is eluted with water. The fractions exhibiting amylase inhibitory activity are collected, concentrated and lyophilized to obtain a powder consisting mainly of Trestatin A, Trestatin B and Trestatin C as shown by high speed liquid chromatography. The solution of said Trestatins in water is passed through a column filled with a cation exchange resin, such as Amberlite CG 50 (a mixture of H-form and ammonium-form, the trade name of Rohm and Haas Co.). The preferred ratio of H-form to ammoniumform lies in the range of 1:9 (v/v)–9:1 (v/v). The column is eluted with water yielding Trestatin B, Trestatin A and Trestatin C in that order. Each Trestatin thus obtained is subjected to rechromatography to yield pure Trestatin A, Trestatin B and Trestatin C respectively. These Trestatins can be, if necessary, converted into various pharmaceutically acceptable salts thereof such as the hydrochloride, sulfate, phosphate, acetate, oxalate, and the like. The Trestatins can be utilized in their salt forms with any conventional pharmaceutically acceptable acid.

Melting point of the hydrochlorides:
Trestatin A hydrochloride:
  163°–190° C. (decomposition with foaming)
Trestatin B hydrochloride:
  158°–186° C. (decomposition with foaming)
Trestatin C hydrochloride:
  190°–200° C. (decomposition with foaming)
Specific rotation of the hydrochlorides:
Trestatin A hydrochloride:
  $[\alpha]_D^{25} = +162.5°$ (c=1.0, 0.01 N HCl)
Trestatin B hydrochloride:
  $[\alpha]_D^{26} = +169°$ (c=1.0, 0.01 N HCl)
Trestatin C hydrochloride:
  $[\alpha]_D^{25} = +160.5°$ (c=1.0, 0.01 N HCl)
Titration (in water):

|  | pKa' | Equivalent |
| --- | --- | --- |
| Trestatin A | 5.0 | 720 |
| Trestatin B | 5.0 | 960 |
| Trestatin C | 5.0 | 650 |

These data coupled with molecular weight data as given above indicate that Trestatin A, B and C are diacidic, monoacidic and triacidic bases, respectively.

Empirical formula:
Trestatin A: $C_{56}H_{94}N_2O_{40}$
Trestatin B: $C_{37}H_{63}NO_{28}$
Trestatin C: $C_{75}H_{125}N_3O_{52}$ The proton magnetic resonance spectra (in $D_2O$ at 100 MHz) of Trestatins A, B and C as the free base were taken with a JEOL FX-100 spectrometer in a homo gated decoupling method (irradiation at δ 4.71 ppm) using DSS as an internal standard and are shown in FIGS. 4, 5 and 6, respectively.

Thin-layer chromatography:
Plate: silica gel $F_{254}$ (Merck)
Solvent system: chloroform-methanol-25% aqueous ammonia-water (1:4:2:1)
Detection: hot sulfuric acid
Under the above described conditions, Rf values of Trestatins A, B and C are 0.19, 0.28 and 0.14, respectively.

High speed liquid chromatography:
Column: μ-Bondapak/CH (1 feet×0.25 inch, Waters Co., USA)

Solvent: acetonitrile-water (63.37)
Flow rate: 4.0 ml/min
Detection: UV absorption at 210 nm Under the above described conditions, the retention times of Trestatins A, B and C are 5.5, 3.4 and 8.8 min., respectively. The chromatograms are shown in FIG. 7.

Paper electrophoresis:
Paper: Toyo Roshi No. 51
Buffer: formic acid-acetic acid-water (25:75:900, pH 1.8)
Voltage: 3,000 V
Time: 40 min.

Under the above described conditions, all of Trestatins move to cathode: Trestatin A by 12 cm, Trestatin B by 9 cm, and Trestatin C by 13 cm.

Structural constituents:

Upon hydrolysis with 4 N hydrochloric acid at 80° C. for 3 hrs., the Trestatins A, B and C yield both glucose and an amine. The amine has pKa' of 3.9 and molecular formula of $C_{13}H_{21}NO_7$, as derived from the high resolution mass spectrum. The Trestatins A, B and C contain 5, 4 and 6 moles of glucose, respectively. Mild acid hydrolysis (80° C., 4 hrs.) of Trestatins A, B or C using Dowex 50 (H-form) as the catalyst gives trehalose ($\alpha$-D-glucopyranosyl-$\alpha$-D-glucopyranoside). None of the Trestatins A, B and C contain amino acids.

From the properties mentioned above, it is considered that the Trestatins A, B and C obtained according to the present invention are weakly basic aminoglucosides having trehalose as the common structural constituents. Based on the above findings, the following structures are proposed for Trestatins A and B (FIG. 8)

Furthermore, Trestatin A, Trestatin B and Trestatin C have high amylase inhibitory activities as shown below and are useful as amylase inhibitors.

Conventional amylase inhibitors which are produced by means of fermentation, have hitherto been reported as follows:

(1) Nojirimycin of Niwa et al. (Agr. Biol. Chem., 34, 966, 1970)

Nojirimycin is a monosaccharide and hence is clearly different from the Trestatins of the present invention.

(2) Peptide sugar of S. Ueda et al. (Agr. Biol. Chem., 37, 2025, 1973 and Agr. Biol. Chem., 40, 1167, 1976)

The peptide sugar contains amino acids as the structural constituents.

(3) Amylostatin A of S. Murao et al. (Japanese patent application, Kokai 123891/1975)

In this patent specification, it is described that Amylostatin A is not adsorbed on a strongly acidic cation exchange resin in a range of pH 1-14. However, as mentioned above, the Trestatins are adsorbed on such ion-exchange resin.

(4) Amylase inhibitor of K. Ueda et al. (Japanese patent application, Kokai 54990/1976)

This amylase inhibitor has a molecular weight of about 600 which is different from those of Trestatin A, Trestatin B and Trestatin C.

(5) Amino-sugar compounds of W. Frommer et al. (German Pat. No. DT 2,347,782: Japanese patent application, Kokai 53593/1975)

All these compounds are monoacidic bases whereas, Trestatin A is a diacidic base and Trestatin C is triacidic base. Trestatin B while being a monoacidic base has trehalose as a structural constituent and is thus different from the amino sugars of Frommer et al.

Amylase inhibitors containing trehalose constituents have not yet been described.

The biological properties of the Trestatins and their salts are as follows:

(1) Acute toxicity:

Acute toxicity is not observed, even when 500 mg/kg of Trestatin A, Trestatin B and Trestatin C respectively are administered to rats orally (which is 65-700 times the effective dosage).

A Trestatin mixture (corresponding to stage III-powder obtained according to Example 1, -II Isolation 3)-) is well tolerated with the daily dosages up to 8000 mg/kg for 10 days in mice and rats.

(2) Antimicrobial spectrum:

The lack of antimicrobial activity of Trestatin A, Trestatin B, and Trestatin C as determined by an agar-dilution method is seen from the table below:

| Antimicrobial Spectra of Trestatin A, Trestatin B and Trestatin C | | | |
|---|---|---|---|
| Test organisms | Trestatin A | Trestatin B | Trestatin C |
| *E. coli* NIHJ | >100 μg/ml | >100 μg/ml | >100 μg/ml |
| *E. coli* NIHJ SMf | >100 | >100 | >100 |
| *E. coli* NIHJ STf | >100 | >100 | >100 |
| *E. coli* K-12 ML1630 | >100 | >100 | >100 |
| *E. coli* CF17 | >100 | >100 | >100 |
| *E. coli* CF41 | >100 | >100 | >100 |
| *Salmonella typhimurium* IFO12529 | >100 | >100 | >100 |
| *Salmonella paratyphi* B | >100 | >100 | >100 |
| *Citrobacter* | >100 | >100 | >100 |
| *Shigella flexneri* | >100 | >100 | >100 |
| *Klebsiella pneumoniae* PC1602 | >100 | >100 | >100 |
| *Pseudomonas aeruginosa* IFO12689 | >100 | >100 | >100 |
| *Pseudomonas aeruginosa* A3 | >100 | >100 | >100 |
| *Pseudomonas aeruginosa* P2 | >100 | >100 | >100 |
| *Proteus vulgaris* OX19 ATCC6898 | >100 | >100 | >100 |
| *Bordetella bronchiseptica* Aichi 202 | >100 | >100 | >100 |
| *Proteus rettgeri* | >100 | >100 | >100 |
| *Serratia marcescens* IFO12648 | >100 | >100 | >100 |
| *Staphylococcus aureus* FDA209P | >100 | >100 | >100 |
| *Staphylococcus aureus* MS3937 | >100 | >100 | >100 |
| *Staphylococcus aureus* MS9261 | >100 | >100 | >100 |
| *Staphylococcus aureus* Smith | >100 | >100 | >100 |
| *Bacillus subtilis* PCI 219 | >100 | >100 | >100 |
| *Sarcina lutea* ATCC 9341 | >100 | >100 | >100 |
| *Candida albicans* Yu1200 | >100 | >100 | >100 |

-continued

| Antimicrobial Spectra of Trestatin A, Trestatin B and Trestatin C | | | |
|---|---|---|---|
| Test organisms | Trestatin A | Trestatin B | Trestatin C |
| Mycobacterium smegmatis ATCC607 | >100 | >100 | >100 |

(3) Amylase inhibitory activity:

The porcine pancreatic α-amylase inhibitory activity with respect to Trestatin A, Trestatin B, Trestatin C, its salts and mixtures thereof is as follows. Each of said inhibitory activities was determined by the method mentioned above.

| Amylase inhibitors | Inhibitory activities (IU/g) |
|---|---|
| Trestatin complex* | $3.6 \times 10^7$ |
| Trestatin A | $7.1 \times 10^7$ |
| Trestatin B | $1.5 \times 10^6$ |
| Trestatin C | $4.9 \times 10^7$ |
| Trestatin A . HCl | $6.3 \times 10^7$ |
| Trestatin B . HCl | $1.3 \times 10^6$ |
| Trestatin C . HCl | $4.5 \times 10^7$ |

| | Inhibition of hyperglycemia induced by cooked rice starch | |
|---|---|---|
| | Rats $ED_{20}$** | Mice p.o. |
| | [mg/kg] | |
| Trestatin A | 1.0 | 1.1 |
| Trestatin B | 7.7 | 3.2 |
| Trestatin C | 3.0 | 0.7 |

*Trestatin complex means the specimen obtained according to Example 1, - II Isolation 5) -, which contains Trestatin A, Trestatin B and Trestatin C.
**$ED_{20}$ is defined as the dose causing after 20 minutes a 20 percent decrease of hyperglycemia induced by oral administration of 2 g/kg body weight cooked rice starch.

Furthermore, these Trestatins can also inhibit α-amylase of Bacillus subtilis and Aspergillus oryzae as well as amylo-α-1,4-α-1,6-glucosidase of Aspergillus niger, however they show no inhibitory activity with respect to β-amylase of sweet potatoes.

The digestion of starch, the main carbohydrate in human food, starts with the action of α-amylase. This enzyme is found in saliva and the secret of the pancreas. The pancreatic amylase is mainly responsible for complete starch digestion in the gastro-intestinal tract. It catalyzes the break-down of the carbohydrate polymer resulting finally in maltose, which is hydrolyzed by intestinal disaccharidases into glucose. Therefore shortly after a meal consisting of starch containing food a marked hyperglycemia leading to hyperinsulinemia is observed.

It is known that in diabetics this hyperglycemia is very pronounced and highy undesirable. In obese people this hyperglycemia is often accompanied by increased insulin secretion, which may lead to an exhaustion of the pancreatic β-cell. In addition hyperinsulinemia favours lipogenesis which contributes to hyperlipidemia.

Trestatin A, B and C as well as preparations containing one or more of these Trestatins can reduce postprandial hyperglycemia and hyperinsulinemia as shown in experiments with rats and mice in starch-loading experiments (page 25 and Tab. 1) or after administration of chow. (Tab. 2)

Reduction of hyperglycemia induced by oral sucrose (Tab. 1) is indicative for some inhibition of sucrase beside its inhibition of α-amylase.

(There is no effect on glucose-induced hyperglycemia).

Therefore the Trestatins of this invention are useful for the treatment of diabetes, obesity, hyperlipidemia and atherosclerosis.

Since salivary α-amylase can contribute to caries by digesting starch orally, Trestatins can also be used for prevention or reduction of caries formation.

In addition Trestatins can be used as biochemical reagents.

TABLE 1

| Effect of Trestatin on hyperglycemia (hyperinsulinemia) following an oral load of native starch or sucrose | | | | |
|---|---|---|---|---|
| | | starch - load | | sucrose - load |
| | dose/kg | glucose | insulin | glucose |
| Trestatin mixture(*) | 6 600 IU | 75 *** | 61 * | — |
| | 22 000 IU | 60 *** | 59 * | — |
| | 66 000 IU | 56 *** | 41 ** | — |
| | 220 000 IU | — | — | 90 * |
| | 660 000 IU | — | — | 73 *** |
| | 2 200 000 IU | — | — | 64 *** |
| Trestatin A | 0.3 mg | 68 *** | 66 * | — |
| | 1.0 mg | 56 *** | 42 *** | — |
| | 3.0 mg | 55 *** | 42 *** | — |
| | 30.0 mg | — | — | 84 * |
| Trestatin C | 0.3 mg | 71 *** | 51 ** | — |
| | 1.0 mg | 60 *** | 51 ** | — |
| | 3.0 mg | 58 *** | 63 ** | — |
| | 30.0 mg | — | — | 85 * |

*Corresponding to stage IV-powder obtained according to Example 1, -II Isolation 4)- which contains Trestatin A, Trestatin B and Trestatin C.
[Plasma Glucose and insulin 20 min. after carbohydrate ± Trestatin (1.6 g wheat starch/kg or 3.2 g sucrose/kg)]
Results in percent of carbohydrate primed controls (* ($p < 0.05$),  ($p < 0.01$), * ($p < 0.001$) according to Kolmogorov-Smirnov-Test)

TABLE 2

| Effect of Trestatin on hyperglycemia and hyperinsulinemia following oral administration of chow | | | | | | |
|---|---|---|---|---|---|---|
| | Plasma Glucose in mg/100 ml (mean ± S.E.) | | | Plasma insulin in μU/ml (mean ± S.E.) | | |
| Dose/rat | 20 min. | 60 min. | 120 min. | 20 min. | 60 min. | 120 min. |
| Chow (control) | 275 ± 9 | 228 ± 11 | 191 ± 6 | 59 ± 10 | 44 ± 10 | 30 ± 5 |
| Chow + 22 440 IU | 205 ± 9 ** | 190 ± 14 * | 184 ± 4 | 15 ± 2 ** | 18 ± 3 | 17 ± 2 |
| Chow + 67 320 IU | 197 ± 2 ** | 173 ± 5 ** | 175 ± 3 * | 22 ± 8 * | 14 ± 1 ** | 13 ± 1 * |
| Chow + 224 400 IU | 189 ± 5 | 164 ± 2 | 169 ± 2 | 18 ± 3 | 8 ± 1 | 9 ± 1 |

TABLE 2-continued

Effect of Trestatin on hyperglycemia and hyperinsulinemia following oral administration of chow

| Dose/rat | Plasma Glucose in mg/100 ml (mean ± S.E.) | | | Plasma insulin in μU/ml (mean ± S.E.) | | |
|---|---|---|---|---|---|---|
| | 20 min. | 60 min. | 120 min. | 20 min. | 60 min. | 120 min. |
| | ** | ** | * | * | ** | ** |

Groups of 6 female rats (85–95 g), starved for 24 hrs, received chow *) by stomach tube (2.2 g/6 ml/rat) ± Trestatin mixture**
* normal lab chow powder (Nafag 859/850, mesh 80; NAFAG, Gossau SG, Switzerland), suspended in 0.07 percent carageenan
** corresponding to stage IV powder obtained according to Example I, -II Isolation 4) - which contains Trestatin A, Trestatin B and Trestatin C.
[Statistics according to Kolmogorov-Smirnov *($p < 0.05$),  ($p < 0.01$), * ($p < 0.001$)]

The novel Trestatins and their salts provided by the invention can find use as medicaments, for example in the form of pharmaceutical preparations which contain them or their salts in admixture with an organic or inorganic inert carrier material suitable for enteral application, such as for example water, gelatine, gum arabic, lactose, starch, magnesium stearate, talc, vegetable oils, polyalkylene glycols etc. The pharmaceutical preparations can be present in solid form, e.g. as tablets, dragees or capsules, or in liquid form, e.g. as solutions, or suspensions.

A dose unit may contain 20 to 50 mg of active ingredient. The daily dosage for an adult can be in the range from 10 to 200 mg and may be varied according to individual requirements.

The Trestatins and their salts may also be used as additives to foodstuffs and dietary preparations such as sugar, fruit juice, chocolate, jam, potato products, flour and products prepared therefrom such as pastry or bread.

Suitably, such foodstuffs or preparations contain 0.1 to 1 percent by weight of the Trestatins of this invention.

The following Examples further illustrate the invention.

EXAMPLE 1

I. Fermentation

A nutrient medium was prepared from the following materials:

| | |
|---|---|
| Potato starch | 20 g |
| Glucose | 20 g |
| Yeast extract | 5 g |
| Sodium chloride | 2.5 g |
| Mineral stock solution *1 | 1 ml |
| Deionized water | 1 liter |

*1 The solution contains $ZnSO_4 \cdot 7H_2O$ (50 g), $CuSO_4 \cdot 5H_2O$ (5 g) and $MnCl_2 \cdot 4H_2O$ (5 g) per liter of deionized water.

The pH of the above mixture was adjusted to 6 with 6 N sodium hydroxide and then 3.2 g of calcium carbonate and 20 g of soybean meal were added followed by steam sterilization at 120° C. for 20 minutes.

The scraped spores from an agar slant of *Streptomyces dimorphogenes* sp. NR-320-OM7HB (FERM-P No. 3664) were used to inoculate ten 500 ml Erlenmeyer flasks containing 110 ml each of the above sterilized medium. The flasks were placed on a rotary shaker operating at 185 r.p.m. and agitated for 72 hours at 27° C. At the end of this time, the flask inocula were used to seed a 50 liter fermentor containing 25 liters of the same medium. The fermentation cycle was about 43 hours during which time the temperature was maintained at 27° C., filtered air was supplied at a rate of 25 liters per minute and agitation was at a rate of 300 r.p.m. A typical Trestatin fermentation beer (pH 6.9) had an activity of $3.1 \times 10^4$ IU/ml.

II. Isolation (1) Carbon adsorption:

Whole beer from the Trestatin fermentation described above was adjusted to pH 7.0 with 5 N sodium hydroxide, and then filtered. To the filtrate (19 liters, $3.1 \times 10^4$ IU/ml, $5.9 \times 10^8$ IU/total) was added 380 g of activated carbon, and the mixture was stirred at room temperature for 20 min., and then filtered. The carbon cake was washed with 4 liters of tap water and suspended in 10 liters of hot 50% aqueous acetone. The suspension was adjusted to pH 2 with 6 N HCl, then kept at 60° C. for 20 min. with stirring, during which time the mixture was kept at pH 2 by occasional addition of 6 N HCl. The mixture was filtered and the carbon cake was treated again with an additional 10 liters of 50% aqueous acetone in a similar manner. The combined filtrate was adjusted to pH 7.0 with 6 N NaOH and filtered to remove a small amount of precipitate formed. The filtrate ($5.6 \times 10^8$ IU/total) was concentrated under reduced pressure to a volume of about 3 liters. A part of the concentrate was lyophilized to give crude Trestatin complex as dark brown powder ($3.2 \times 10^6$ IU/g), herein designated as Stage I powder.

(2) Dowex 50 adsorption:

The concentrate (approx. 3 liters, $5.6 \times 10^8$ IU/total), as described above, was passed through a column (80×7.5 cm) of Dowex 50 (H-form, 3.5 liters 20–50 mesh) at a rate of approx. 10 ml/min. The column was washed with 10.5 liters of deionized water, eluted with 1 N $NH_4OH$ and fractionated. Fractions containing more than $3 \times 10^3$ IU/ml of Trestatin were combined, concentrated under reduced pressure and lyophilized to give 75.4 g of brown powder ($7.0 \times 10^6$ IU/g, $5.3 \times 10^8$ IU/total), herein designated as Stage II powder.

(3) Methanol treatment:

Stage II powder (75.4 g, $7.0 \times 10^6$ IU/g, $5.3 \times 10^8$ IU/total), as described above, was suspended in 3,770 ml of methanol, and the mixture was stirred at room temperature for 2 hrs. The insoluble part was collected by filtration, washed with small amounts of methanol and dried to give 41.5 g of brown powder ($1.1 \times 10^7$ IU/g, $4.6 \times 10^8$ IU/total), herein designated as Stage III powder.

(4) Dowex 1 chromatography:

Stage III powder (41.5 g, $1.1 \times 10^7$ IU/g, $4.6 \times 10^8$ IU/total), as described above, was dissolved in 100 ml of deionized water. The solution was applied onto a column (87×5.5 cm) of Dowex 1 (acetate-form, 2,050 ml, 200–400 mesh). The column was developed with deionized water at a flow rate of 2.5 ml/min. and the eluate was fractionated (each fraction: 17 ml).

The active fractions 35–70 were combined, concentrated under reduced pressure and lyophilized to give 22.6 g of a yellow powder ($1.8 \times 10^7$ IU/g, $4.1 \times 10^8$ IU/total), herein designated as Stage IV powder.

(5) Dowex 50 chromatography:

The Stage IV powder (22.6 g, $1.8 \times 10^7$ IU/g, $4.1 \times 10^8$ IU/total), as described above, was dissolved in 50 ml of deionized water, and the solution was applied onto a column ($85 \times 6.6$ cm) of Dowex 50 (ammonium-form, 2,900 ml, 200–400 mesh). The column was eluted with deionized water at a flow rate of 2.5 ml/min., and the eluate was fractionated (each 17 ml). The active fractions 65–89 were combined, concentrated under reduced pressure and lyophilized to give 10.6 g of Trestatin complex as a pale yellow powder ($3.6 \times 10^7$ IU/g, $3.8 \times 10^8$ IU/total), herein designated as Stage V powder.

III. Separation of Trestatin complex into Trestatins A, B and C

The Stage V powder (10.6 g, $3.6 \times 10^7$ IU/g, $3.8 \times 10^8$ IU/total), as described above, was dissolved in 20 ml of distilled water, and the solution was applied onto a column ($78 \times 4.8$ cm) of Amberlite CG 50 (a mixed bed consisting of 3.5 parts of ammonium-form and 6.5 parts of H-form, 1,420 ml, type I). The column was eluted with distilled water at a flow rate of 2.0 ml/min., and the eluate was fractionated (each fraction: 14 ml). The active fractions were examined by high speed liquid chromatography (HSLC) under the following conditions:

| Column: | μ Bondapak/Carbohydrate ($\frac{1}{4}"\times 1'$, Waters Associate) |
|---|---|
| Carrier: | $CH_3CN:H_2O$ (63:37) |
| Flow rate: | 4.0 ml/min. |
| Injection volume: | 2–10 μl |
| Detection: | Ultraviolet absorption at 210 nm |

The appropriate fractions were combined, concentrated under reduced pressure and lyophilized. The results are shown below.

| Fraction No. | Residue weight (g) | Activity (IU/g) | Major component (retention time on HSLC) |
|---|---|---|---|
| 71–90 | 1.40 | $9.4 \times 10^6$ | Trestatin B (3.4 min.) |
| 131–165 | 1.88 | $5.9 \times 10^7$ | Trestatin A (5.5 min.) |
| 311–380 | 0.79 | $4.4 \times 10^7$ | Trestatin C (8.8 min.) |

IV. Preparation of Trestatin A

A pure sample of Trestatin A was prepared by rechromatography on Amberlite CG 50. Accordingly, a 1.17 g sample of Trestatin A obtained as in Item III was dissolved in 4 ml of distilled water and applied onto a column ($133 \times 1.7$ cm) of Amberlite CG 50 (a mixed bed consisting of 8 parts of H-form resin and 2 parts of ammonium-form resin, 300 ml, type II). The column was eluted with distilled water, and the eluate was fractionated (each fraction: 7 ml) and monitored by high speed liquid chromatography under the conditions described above. Fractions 245–465 containing Trestatin A were combined, concentrated under reduced pressure and lyophilized to give 649 mg of Trestatin A as a white powder having the properties indicated above.

V. Preparation of Trestatin B

A pure sample of Trestatin B was prepared by rechromatography on Amberlite CG 50. Accordingly, a 450 mg sample of Trestatin B obtained as in Item III was dissolved in 2 ml of distilled water and applied onto a column ($122 \times 1.7$ cm) of Amberlite CG 50 (a mixed bed consisting of 8 parts of H-form resin and 2 parts of ammonium-form resin, 280 ml, type II). The column was eluted with distilled water, and the eluate was fractionated (each fraction: 3 ml) and monitored by high speed liquid chromatography under the conditions described above. Fractions 121–129 containing Trestatin B were combined, concentrated under reduced pressure and lyophilized to give 170 mg of Trestatin B as a white powder having the properties given above.

VI. Preparation of Trestatin C

A pure sample of Trestatin C was prepared by rechromatography on Amberlite CG 50. Accordingly, a 720 mg sample of Trestatin C obtained as in Item III was dissolved in 3 ml of distilled water and applied onto a column ($133 \times 1.7$ cm) of Amberlite CG 50 (a mixed bed consisting of 6.2 parts of H-form resin and 3.8 parts of ammonium form resin, 300 ml, type II). The column was eluted with distilled water, and the eluate was fractionated (each fraction: 6 ml) and monitored by high speed liquid chromatography under the conditions described above. Fractions 42–59 containing Trestatin C were combined, concentrated under reduced pressure and lyophilized to give 515 mg of Trestatin C as a white powder having the properties given above.

EXAMPLE 2

Preparation of Trestatin A hydrochloride

Trestatin A (95 mg) obtained as in Example 1 was dissolved in 1 ml of distilled water and the pH was adjusted to 2.0 with 0.1 N hydrochloric acid. The solution was concentrated under reduced pressure to a volume of about 0.5 ml. Ethanol (6 ml) was added, forming a white precipitate which was collected by centrifugation, washed with 2 ml of ethanol and dried in vacuo, giving 97 mg of Trestatin A dihydrochloride as a white powder.

EXAMPLE 3

Preparation of Trestatin B hydrochloride

Trestatin B (92 mg) obtained as in Example 1 was dissolved in 1 ml of distilled water and the pH was adjusted to 2.0 with 0.1 N hydrochloric acid. The solution was concentrated under reduced pressure to a volume of about 0.5 ml. Ethanol (7 ml) was added, forming a white precipitate which was collected by centrifugation, washed with 2 ml of ethanol and dried in vacuo, giving 91 mg of Trestatin B monohydrochloride as a white powder.

EXAMPLE 4

Preparation of Trestatin C hydrochloride

Trestatin C (90 mg) obtained as in Example 1 was dissolved in 1 ml of distilled water and the pH was adjusted to 2.0 with 0.1 N hydrochloric acid. The solution was concentrated under reduced pressure to a volume of about 0.5 ml. Ethanol (6 ml) was added, forming a white precipitate which was collected by centrifugation, washed with 2 ml of ethanol and dried in vacuo, giving 91 mg of Trestatin C trihydrochloride as a white powder.

EXAMPLE 5

In a procedure similar to the one described in Example 1 except that *Streptomyces dimorphogenes* sp. NR-320-OM7HBS (FERM-P No. 3665) was utilized, Trestatin A, Trestatin B and Trestatin C were obtained respectively.

4. Brief Explanation of the Drawings

What we claim is:

1. The novel amino sugar derivatives Trestatin A, Trestatin B and Trestatin C and salts and mixtures thereof having trehalose as a common structural feature and having the following properties:

(a) Elementary analysis:

|  | C % | H % | N % | O % |
|---|---|---|---|---|
| Trestatin A: | 46.72 | 7.13 | 2.08 | 43.28 |
| Trestatin B: | 46.27 | 7.04 | 1.65 | 44.69 |
| Trestatin C: | 47.55 | 7.15 | 2.29 | 42.66 |

(b) Molecular weight (Osmometry):
 Trestatin A: 1470
 Trestatin B: 975
 Trestatin C: 1890

(c) Melting point:
 Trestatin A: 221°-232° C. (dec.)
 Trestatin B: 209°-219° C. (dec.)
 Trestatin C: 230°-237° C. (dec.)

(d) Specific rotation:
 Trestatin A: $[\alpha]_D^{24} = +177°$ (c=1.0, H$_2$O)
 Trestatin B: $[\alpha]_D^{26} = +187°$ (c=1.0, H$_2$O)
 Trestatin C: $[\alpha]_D^{23} = +169.5°$ (c=1.0, H$_2$O)

Figure 1:
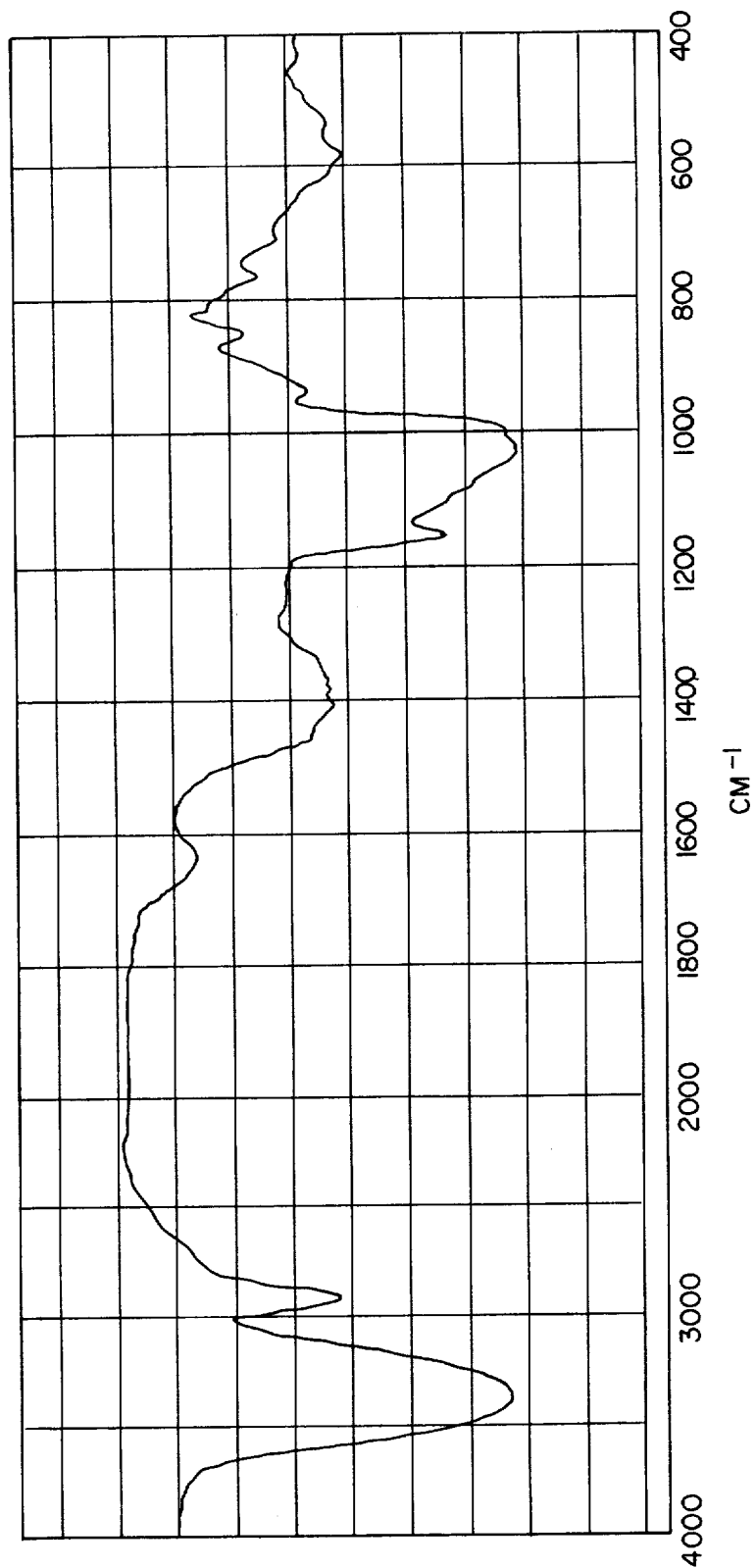
FIGS. 1, 2 and 3 show the Infrared absorption spectra of Trestatin A, Trestatin B and Trestatin C respectively.
Figure 2:
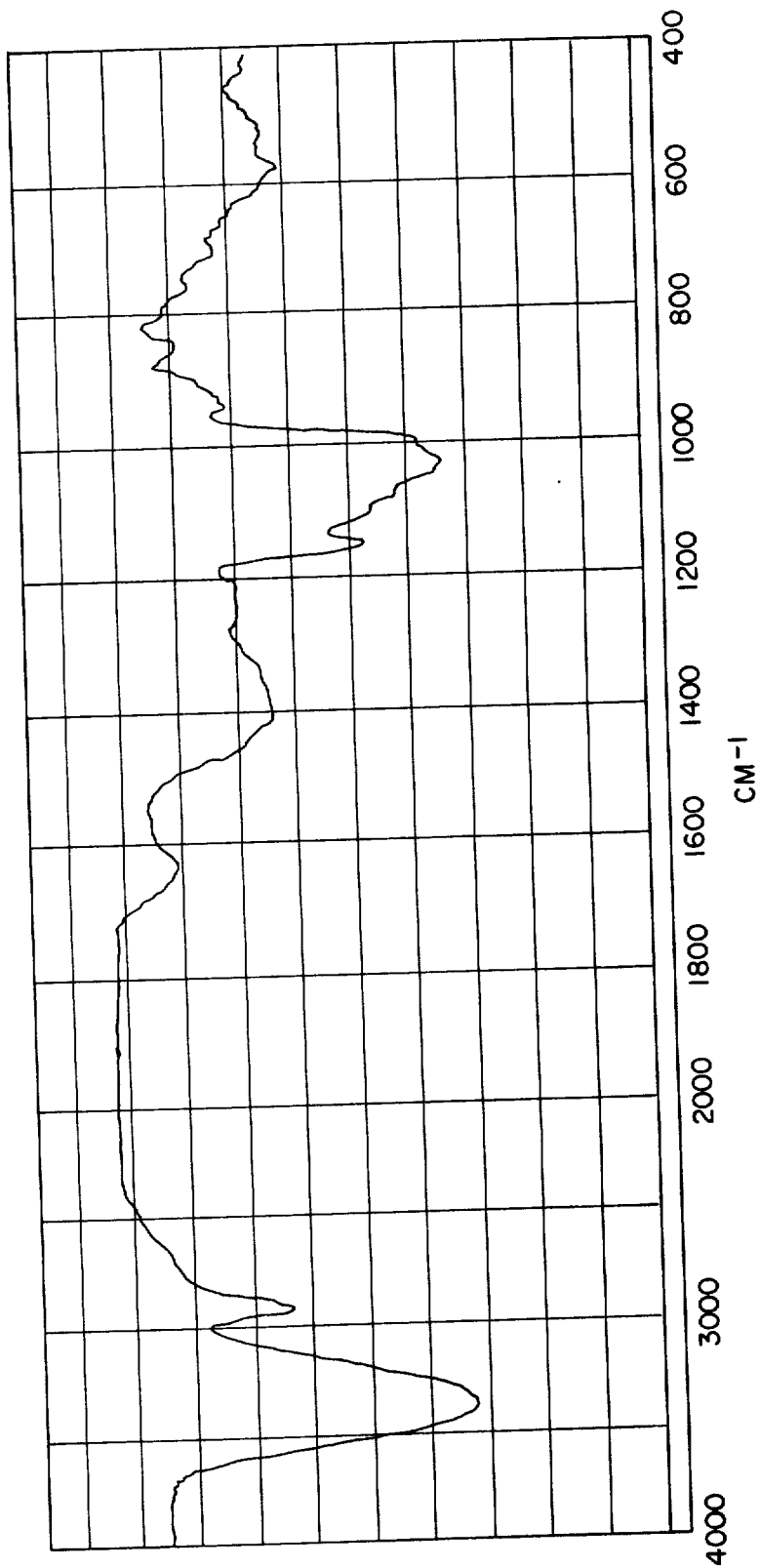
Figure 3:
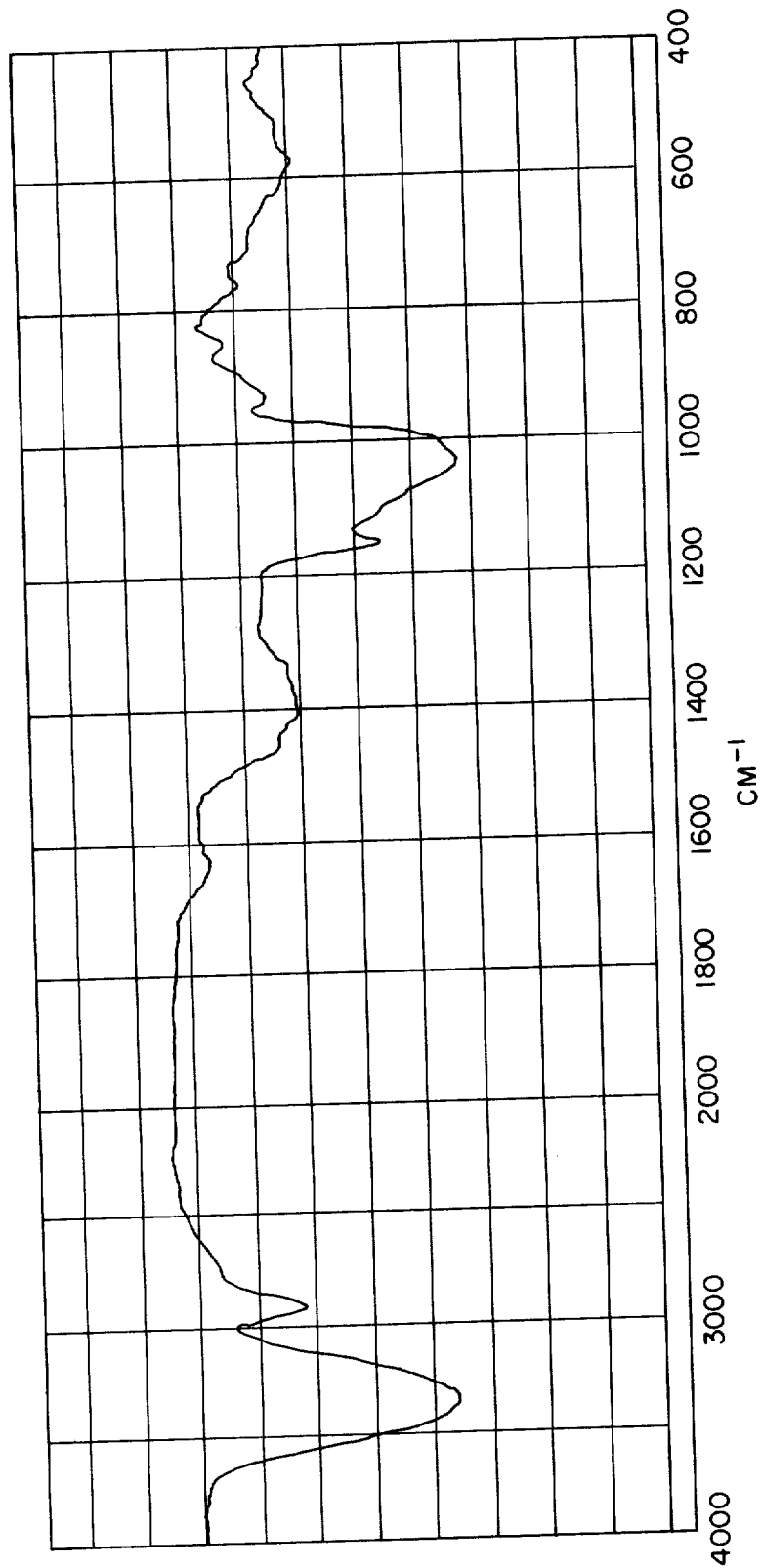

(e) Ulraviolet absorption spectrum (in water):
 Each of Trestatin A, Trestatin B and Trestatin C shows end absorption (f) Infrared absorption spectrum (in KBr):
 Trestatin A: as shown in FIG. 1
 Trestatin B: as shown in FIG. 2
 Trestatin C: as shown in FIG. 3

Figure 4:
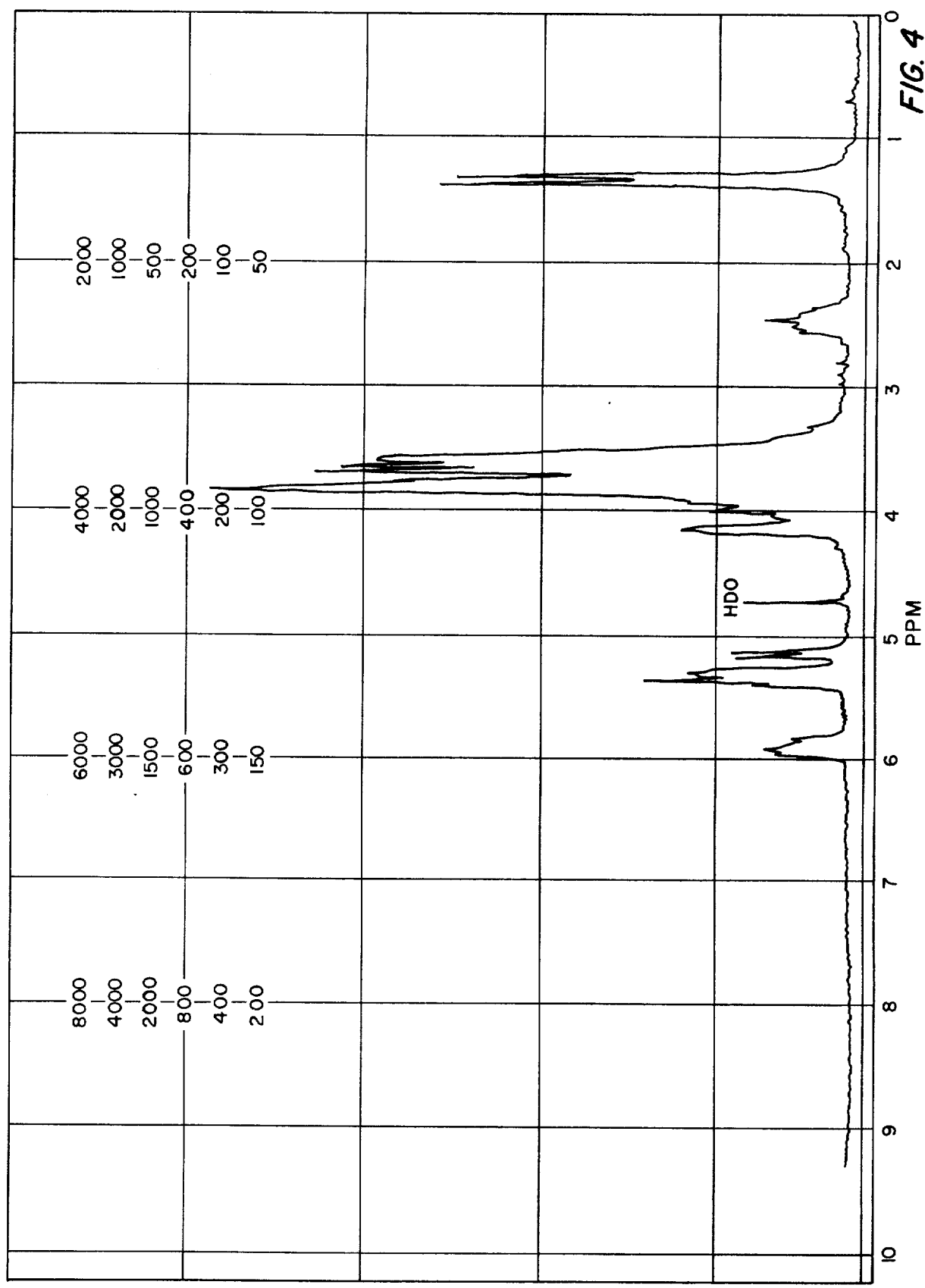
FIGS. 4, 5 and 6 show the $^1$H NMR spectra (in D$_2$O at 100 MHz) of Trestatin A, Trestatin B and Trestatin C respectively.
Figure 5:
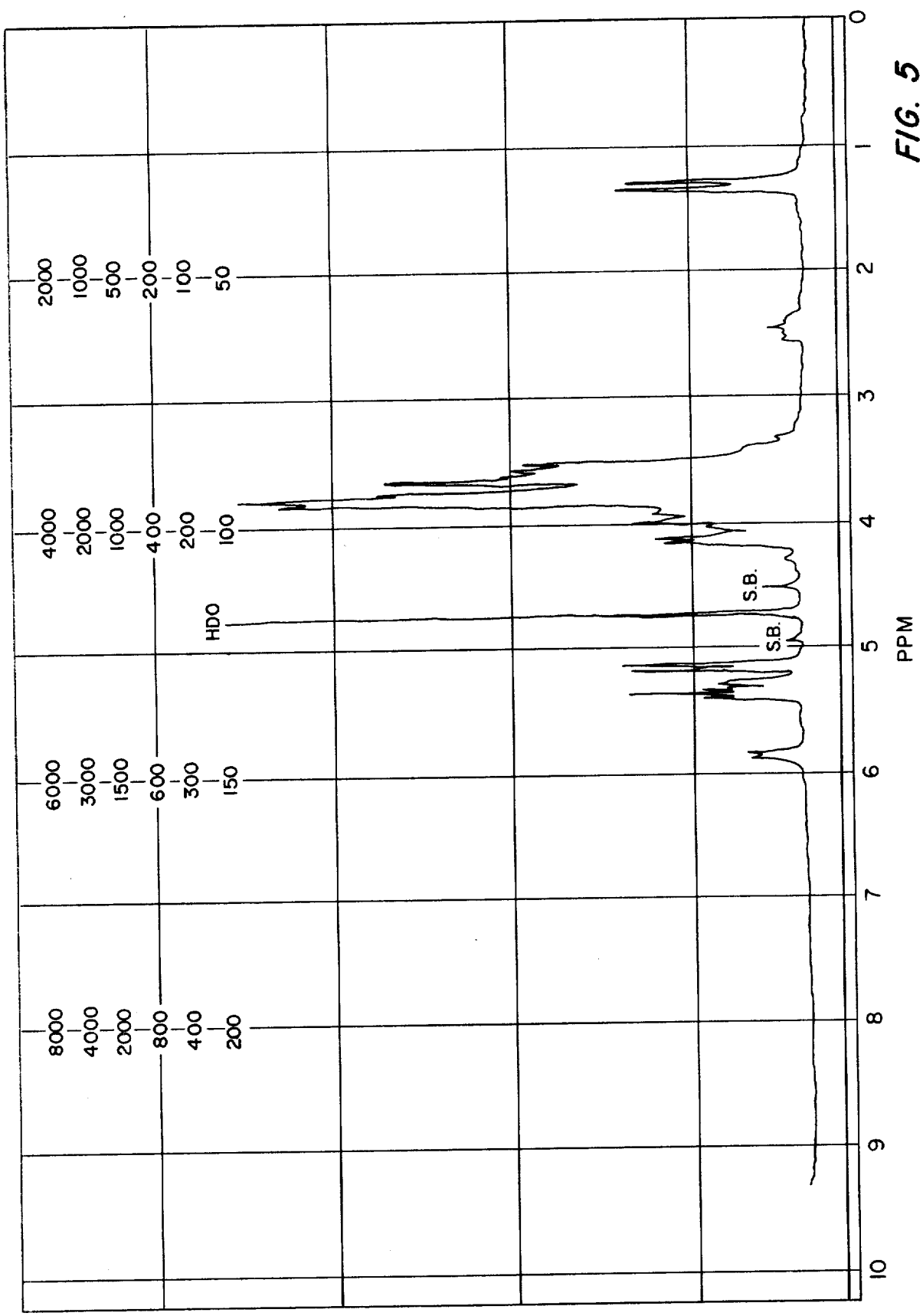
Figure 6:
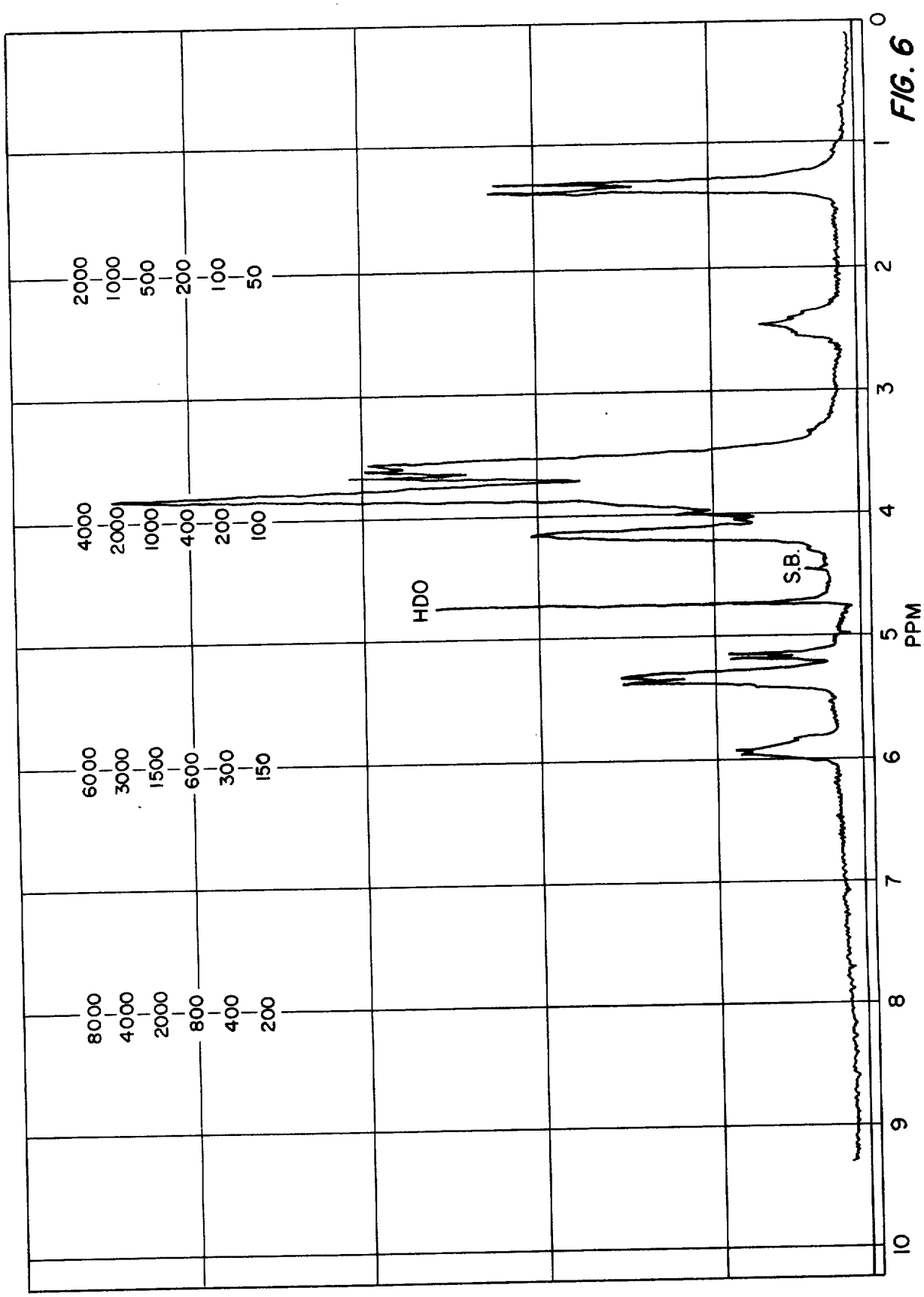
Figure 7:
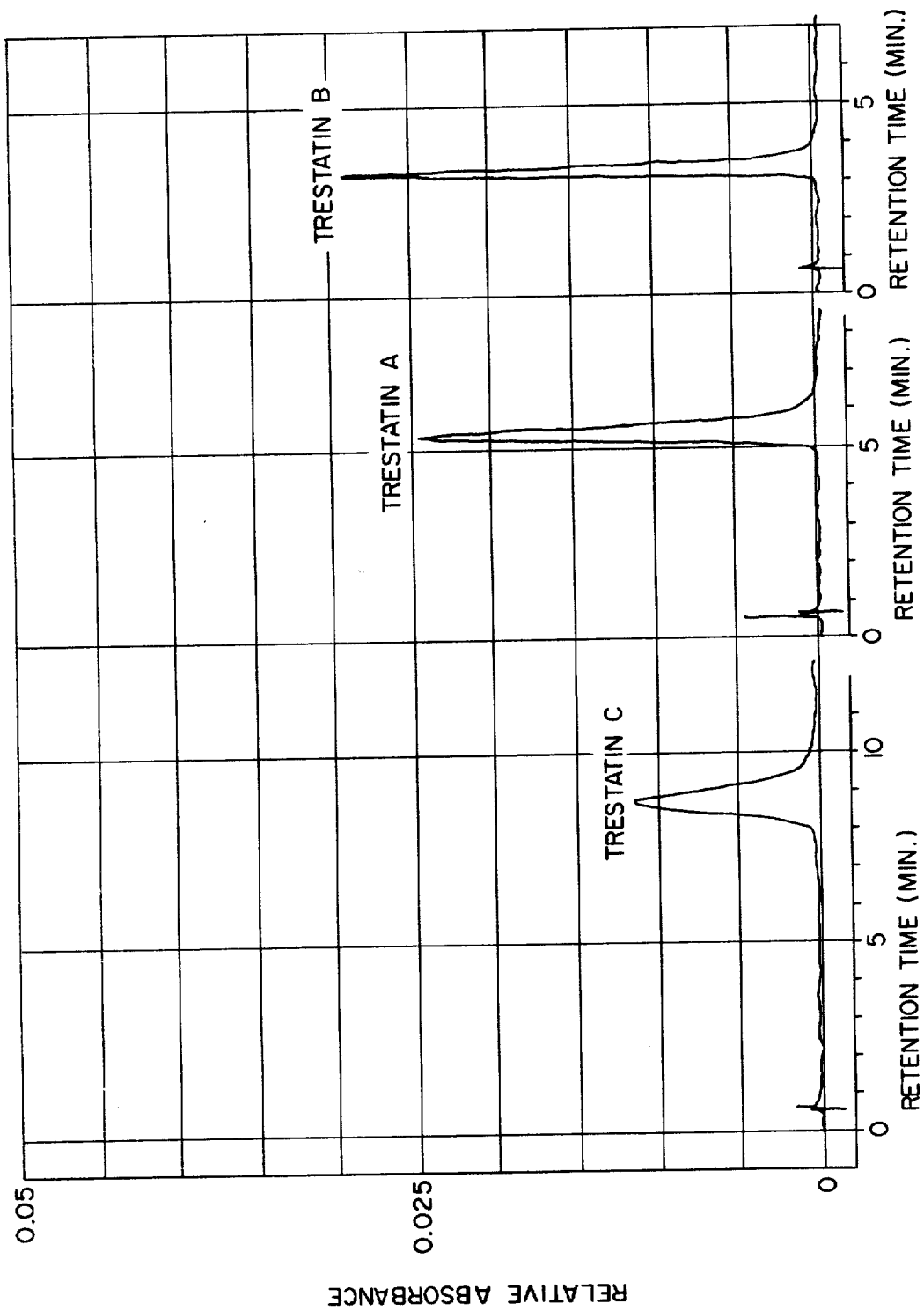
FIG. 7 shows the high speed liquid chromatograms of Trestatin A, Trestatin B and Trestatin C respectively.
Figure 8:
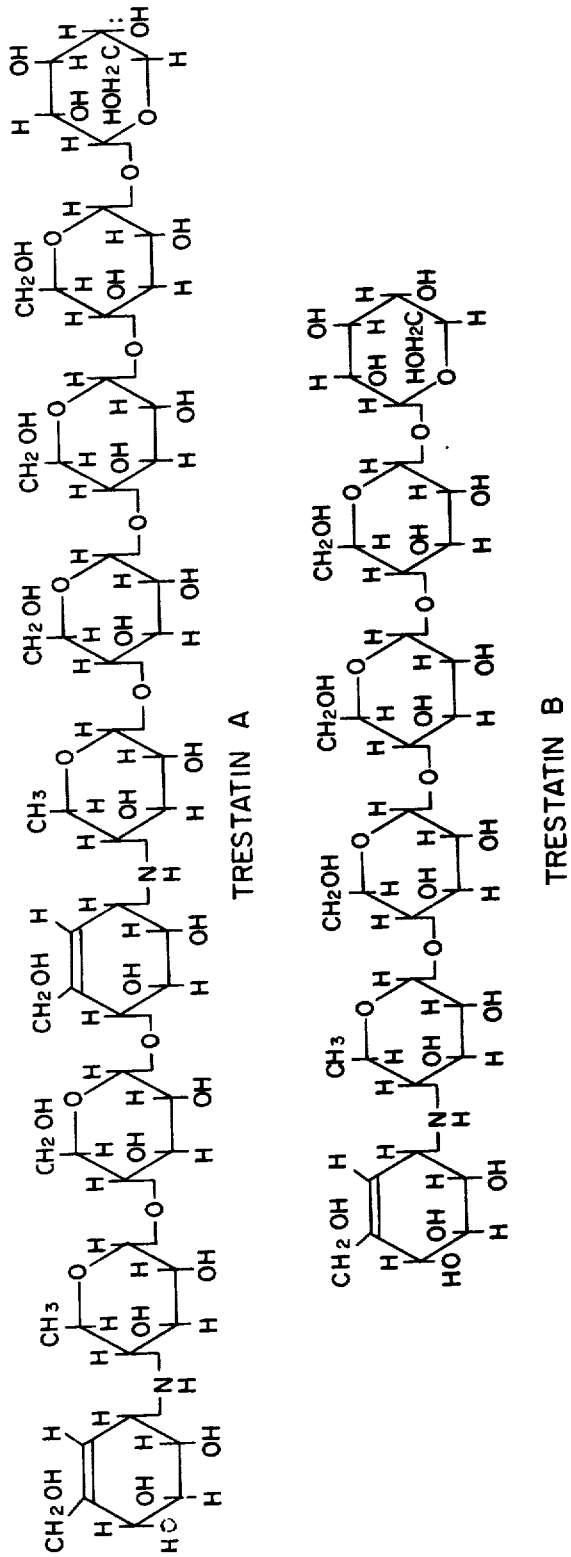

(g) $^1$H NMR spectrum (in D$_2$O at 100 MHz):
 Trestatin A: as shown in FIG. 4
 Trestatin B: as shown in FIG. 5
 Trestatin C: as shown in FIG. 6

(h) Solubility in solvents:
 Trestatin A, Trestatin B and Trestatin C and their hydrochlorides are easily soluble in water; soluble in dimethylsulfoxide; slightly soluble in ethanol and acetone; and insoluble in ethyl acetate and chloroform;

(i) Color reaction:
 Each of Trestatin A, Trestatin B and Trestatin C is positive to permanganate and anthrone reactions, and negative to Sakaguchi reaction.

2. Amylase inhibiting compositions containing Trestatin A, Trestatin B or Trestatin C as defined in claim 1, or a salt of mixtures thereof in admixture with an organic or inorganic inert carrier material suitable for enteral application.

* * * * *